(12) United States Patent
Reznikoff et al.

(10) Patent No.: US 7,608,434 B2
(45) Date of Patent: Oct. 27, 2009

(54) MUTATED TN5 TRANSPOSASE PROTEINS AND THE USE THEREOF

(75) Inventors: William S. Reznikoff, Fitchburg, WI (US); Richard J. Gradman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 330 days.

(21) Appl. No.: 11/195,113

(22) Filed: Aug. 2, 2005

(65) Prior Publication Data

US 2006/0040355 A1 Feb. 23, 2006

Related U.S. Application Data

(60) Provisional application No. 60/598,800, filed on Aug. 4, 2004.

(51) Int. Cl.
*C12N 15/66* (2006.01)
*C12N 9/00* (2006.01)

(52) U.S. Cl. .................. 435/91.41; 435/183; 435/194; 435/91.52

(58) Field of Classification Search ........................ None
See application file for complete search history.

(56) References Cited

U.S. PATENT DOCUMENTS

| | | | |
|---|---|---|---|
| 5,925,545 | A | 7/1999 | Reznikoff et al. |
| 5,948,622 | A | 9/1999 | Reznikoff et al. |
| 5,965,443 | A | 10/1999 | Reznikoff et al. |
| 6,159,736 | A | 12/2000 | Reznikoff et al. |
| 6,406,896 | B1 | 6/2002 | Reznikoff et al. |
| 6,437,109 | B1 | 8/2002 | Reznikoff et al. |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

Zhou and Reznikoff, Tn5 Transposase Mutants that Alter DNA Binding Specificity, J. Mol. Biol., vol. 271, pp. 362-373, 1997.*
Ahmed A. & Podemski L., The Revised Sequence of TN5. Gene 154:129-130 (1995).
Goryshin I. & Reznikoff W., Tn5 in Vtro Transposition. J. Biol. Chem. 273:7367-7374 (1998).
Jilk R., et al., The Organization of the Outside End of Transposon Tn5. J. Bacteriol. 178:1671-1679 (1996).
Krebs M. & Reznikoff W., Use of a Tn5 Derivative That Creates lacZ Translational Fusions to Obtain a Transposition Mutant. Gene 63:277-285 (1988).
Reznikoff W., et al., Tn5: A Molecular Window on Transposition. Biochem. Biophys. Res. Commun. 266:729-34 (1999).
Rezsohazy R., et al., The IS4 Family of Insertion Sequences: Evidence for a Conserved Transposase Motif. Mol. Microbiol. 9:1283-1295 (1993).
Wiegand T. & Reznikoff W., Characterization of Two Hypertransposing Tn5 Mutants. J. Bactiol. 174:1229-1239 (1992).
Yin J., et al., Effect of dam Methylation on Tn5 Transposition. J. Mol. Biol. 199:35-45 (1988).
Zhou M., et al., Molecular Genetic Analysis of Transposase-end DNA Sequence Recognition: Cooperatively of Three Adjacent Base-Pairs in Specific Interaction with a Mutant Tn5 Transposase J. Mol. Biol. 276:913-925 (1998).

* cited by examiner

*Primary Examiner*—Richard G Hutson
(74) *Attorney, Agent, or Firm*—Quarles & Brady LLP

(57) ABSTRACT

Transposase proteins that are modified relative to and have higher transposase activities than the wild-type Tn5 transposase are disclosed. A transposase protein of the present invention differs from the wild-type Tn5 transposase at amino acid position 41, 42, 450, or 454 and has greater avidity than the wild-type Tn5 transposase for at least one of a Tn5 outside end sequence as defined by SEQ ID NO:3, a Tn5 inside end sequence as defined by SEQ ID NO:4, and a modified Tn5 outside end sequence as defined by SEQ ID NO:5. Also disclosed are various systems and methods of using the transposase proteins of the present invention for in vitro or in vivo transposition.

15 Claims, No Drawings

US 7,608,434 B2

MUTATED TN5 TRANSPOSASE PROTEINS AND THE USE THEREOF

CROSS-REFERENCE TO RELATED APPLICATIONS

This application claims the benefit of U.S. provisional patent application Ser. No. 60/598,800, filed on Aug. 4, 2004, incorporated by reference in its entirety.

STATEMENT REGARDING FEDERALLY SPONSORED RESEARCH OR DEVELOPMENT

This invention was made with United States government support awarded by the following agency: NIH, Grant No. GM50692. The United States government has certain rights in this invention.

BACKGROUND OF THE INVENTION

Bacterial transposons such as Tn5 evolved within the cell by maintaining a low mobility level. While necessary for the transposon to survive, the low mobility level has inhibited the ability of researchers to detail the molecular transposition process and to exploit the transposition process for use, e.g., in the development of new diagnostic and therapeutic resources. Tn5 is a conservative "cut and paste" transposon of the IS4 family (Rezsohazy, R., Hallet, B., Delcour, J., and Mahillon, J., "The IS4 family of insertion sequences: evidence for a conserved transposase motif," Mol Microbiol. 9:1283-1295 (1993)) that encodes a 53 kD transposase protein (Tnp) that is responsible for its movement. The wild-type Tn5 Tnp amino acid and nucleic acid sequences are known (Ahmed, A. and Podemski, L. The Revised Sequence of Tn5. Gene 154(1), 129-130(1995), incorporated by reference as if set forth herein in its entirety). A nucleic acid sequence that encodes wild-type Tn5 Tnp is provided as SEQ ID NO:1. A polypeptide sequence encoded by SEQ ID NO:1 which corresponds to wild-type Tn5 Tnp is provided as SEQ ID NO:2.

The Tnp facilitates movement of the entire element by binding initially to each of two 19 bp specific binding sequences termed outside end (OE; SEQ ID NO:3,5'-CTGACTCTTATACACAAGT-3'), followed by formation of a nucleoprotein structure termed a synapse, blunt ended cleavage of each end, association with a target DNA, and then strand transfer (Reznikoff, W. S., Bhasin, A., Davies, D. R., Goryshin, I. Y., Mahnke, L. A., Naumann, T., Rayment, I., Steiniger-White, M., and Twining, S. S., "Tn5: A molecular window on transposition," Biochem. Biophys. Res. Commun. 266:729-34 (1999)). Tn5 Tnp can also promote movement of a single insertion sequence by using a combination of OE and inside end (IE; SEQ ID NO:4,5'-CTGTCTCTTGATCAGATCT-3') sequences. The IE is also 19 bp long and is identical to OE at 12 of 19 positions. In vivo, Tn5 Tnp exhibits a marked preference for OE in E. coli. Transposase recognition and binding to IE are inhibited in E. coli by the presence of four dam methylation sites (GATC palindromes) which add four methyl groups per inside end sequence (IE$^{ME}$; also depicted as SEQ ID NO:4, methylation not shown) (Yin, J. C. P., Krebs, M. P., and Reznikoff, W. S., "Effect of dam Methylation on Tn5 Transposition," J. Mol. Biol., 199:35-45 (1988), incorporated by reference as if set forth herein in its entirety). This methylation reduces transposition by reducing protein-DNA primary recognition (Jilk, R. A., York, D., and Reznikoff, W. S., "The organization of the outside end of transposon Tn5," J. Bacteriol. 178:1671-1679 (1996)).

Tn5 transposon also encodes an inhibitor protein that can interfere with transposase activity. The inhibitor-encoding sequence overlaps with the sequence that encodes the transposase. An AUG in the wild-type Tn5 Tnp gene that encodes methionine at transposase amino acid 56 is the first codon of the inhibitor protein. Replacement of the methionine at position 56 with an alanine has no apparent effect upon the transposase activity. However, it prevents translation of the inhibitor protein and thus results in a higher transposition rate. Weigand, T. W. and W. S. Reznikoff, "Characterization of Two Hypertransposing Tn5 Mutants," J. Bact. 174:1229-1239 (1992), incorporated herein by reference.

A principal roadblock to understanding how Tn5 Tnp works is the fact that purified wild-type Tnp has no detectable activity in vitro. Recently, a double mutant hyperactive form of transposase ("Tnp EK/LP") that promotes the transposition reaction in vitro was developed (U.S. Pat. No. 5,965,443, incorporated herein by reference in its entirety). The Tnp EK/LP protein differs from wild-type Tn5 Tnp at position 54 (Glu to Lys mutation) and at position 372 (Leu to Pro mutation), in addition to a non-essential but advantageous change at position 56 that prevents production of the inhibitor protein. The modified hyperactive Tnp protein increases the dramatic preference for OE termini of wild-type Tn5 Tnp. In addition, certain modifications on the OE sequence have been shown to increase the transposition frequency by Tnp EK/LP (U.S. Pat. Nos. 5,925,545 and 6,437,109, both of which are herein incorporated by reference in their entirety). Tnp EK/LP has clarified many aspects of Tn5 transposition that were not previously adequately addressable in vivo.

Another recent development in Tn5 research involves the identification of mutated Tn5 Tnps that preferentially promote transposition with IEs over OEs (U.S. Pat. No. 6,406, 896, which is herein incorporated by reference in its entirety). These mutated Tnps contain a modification relative to the wild-type Tn5 Tnp at amino acid position 58 and can further contain a modification at amino acid position 8, 344, or both. Both unmethylated and methylated IE (IE$^{ME}$) sequences can be used efficiently for transposition by these mutated Tnps.

In vitro polynucleotide transposition is a powerful tool for introducing random or targeted mutations into genomes. Tn5 transposon-based systems useful for this purpose are known in the art (U.S. Pat. Nos. 5,948,622, 6,159,736, and 6,406, 896, all of which are incorporated herein by reference in their entirety). Modified Tn5 Tnps with increased in vitro transposition capability in one or more of the above systems are desirable in the art.

BRIEF SUMMARY OF THE INVENTION

The present invention is summarized in that Tn5 Tnps modified relative to the wild-type enzyme at an amino acid position selected from position 41, position 42, position 450, position 451, or position 454 have higher transposase activities than the wild-type enzyme. These modified Tn5 Tnps have greater avidity than the wild-type Tnp for at least one of a wild-type Tn5 outside end sequence as defined by SEQ ID NO:3, a wild-type Tn5 inside end sequence as defined by SEQ ID NO:4, and a modified Tn5 outside end sequence as defined by SEQ ID NO:5 (5'-CTGTCTCTTATACACATCT-3') and can be used in a variety of in vitro and in vivo transposition applications.

In one aspect, the present invention relates to a polypeptide or isolated polypeptide that comprises the amino acid sequence of a Tnp of the invention. A Tnp of the invention is defined as a modified Tn5 Tnp that comprises a modification relative to the wild-type enzyme at at least one of amino acid positions 41, 42, 450, and 454.

In another aspect, the present invention relates to a nucleic acid or isolated nucleic acid that comprises a nucleotide sequence encoding a Tnp of the present invention. Optionally, the nucleic acid can comprise a transcription control sequence operably linked to the coding nucleotide sequence. A host cell comprising the above nucleic acid is also within the scope of the present invention.

In another aspect, the present invention relates to a method of using a polypeptide comprising a Tnp of the present invention for inter- or intra-molecular transposition in vitro as described in U.S. Pat. No. 5,948,622.

In another aspect, the present invention relates to a method for forming a synaptic complex using a polypeptide comprising a Tnp of the present invention and further introducing the complex into a target cell to make random or quasi-random insertional mutations in the cellular nucleic acid as described in U.S. Pat. No. 6,159,736.

The invention will be more fully understood upon consideration of the following detailed description taken in conjunction with the accompanying drawing.

BRIEF DESCRIPTION OF THE SEVERAL
VIEWS OF THE DRAWINGS

Not applicable.

DETAILED DESCRIPTION OF THE INVENTION

The term "polypeptide" and the term "protein" are used interchangeably in the specification and claims.

The term "isolated polypeptide" or "isolated nucleic acid" used in the specification and claims means a polypeptide or nucleic acid isolated from its natural environment or prepared using synthetic methods such as those known to one of ordinary skill in the art. Complete purification is not required in either case. Amino acid or nucleotide sequences that flank a polypeptide or nucleic acid in nature can but need not be absent from the isolated form. A polypeptide and nucleic acid of the invention can be isolated and purified from normally associated material in conventional ways such that in the purified preparation the polypeptide or nucleic acid is the predominant species in the preparation. At the very least, the degree of purification is such that the extraneous material in the preparation does not interfere with use of the polypeptide or nucleic acid of the invention in the manner disclosed herein. The polypeptide or nucleic acid is preferably at least about 85% pure, more preferably at least about 95% pure, and most preferably at least about 99% pure.

Further, an isolated nucleic acid has a structure that is not identical to that of any naturally occurring nucleic acid or to that of any fragment of a naturally occurring genomic nucleic acid spanning more than three separate genes. The term therefore covers, for example, (a) a DNA that has the sequence of part of a naturally occurring genomic DNA molecule but which is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library. An isolated nucleic acid molecule can be modified or unmodified DNA or RNA, whether fully or partially single-stranded or double-stranded or even triple-stranded. A modified nucleic acid molecule can be chemically or enzymatically induced and can include so-called non-standard bases such as inosine.

It is disclosed here that modifying the wild-type Tn5 Tnp at one or more of the amino acid positions 41, 42, 450, 451, and 454 can increase the transposition activity of the enzyme with at least one of the Tn5 wild-type OE (SEQ ID NO:3), wild-type IE (SEQ ID NO:4), and modified OE (SEQ ID NO:5) sequences. Without intending to be limited by theory, the inventors believe that the above positions are important for keeping the N- and C-terminal domains of the wild-type Tn5 Tnp close to each other to maintain the inactive configuration of the enzyme. Introducing a mutation to one or more of these positions will inhibit the interaction between the N- and C-terminal domains and thus allow the enzyme to stay in an active or more active configuration by keeping the N- and C-terminal domains farther apart. Although the invention was demonstrated in the examples below with mutated Tn5 Tnps generated on the EK54/MA56/LP372 Tn5 background along with OE or IE sequences, the inventors expect similar results with the corresponding mutated Tn5 Tnps generated on the wild-type background and with the modified OE sequence defined by SEQ ID NO:5.

In one aspect, the present invention relates to a Tnp or isolated Tnp that differs from the wild-type Tn5 Tnp at an amino acid position selected from position 41, position 42, position 450, or position 454. The Tnp of the present invention has greater avidity than the wild-type Tn5 Tnp for at least one of the Tn5 OE sequence defined by SEQ ID NO:3, the Tn5 IE sequence defined by SEQ ID NO:4, and the modified Tn5 OE sequence defined by SEQ ID NO:5. Preferably, the modifications relative to the wild-type Tn5 Tnp at the above positions are substitution modifications. Examples of these modifications include but are not limited to tyrosine to alanine or cysteine at position 41, serine to alanine at position 42, tryptophan to cysteine at position 450, and glutamic acid to cysteine at position 454.

Optionally, a Tnp of the present invention further comprises a modification relative to the wild-type Tn5 Tnp at amino acid position 451, 54, 372, or any combination thereof. Examples of modifications at these positions include but are not limited to glutamic acid to cysteine at position 451, glutamic acid to lysine or valine at position 54, and leucine to proline or glutamine at position 372.

A Tnp of the present invention can also optionally comprise a modification relative to the wild-type Tn5 Tnp at amino acid position 56. For example, the methionine at position 56 of the wild-type Tn5 Tnp can be substituted with alanine. Although such a mutation has no apparent effect upon the transposase activity, it prevents translation of a Tn5 Tnp inhibitor protein encoded in partially overlapping sequence with the transposase, leading to a higher transposition rate. Weigand, T. W. and W. S. Reznikoff, "Characterization of Two Hypertransposing Tn5 Mutants," *J. Bact.* 174: 1229-1239 (1992), incorporated herein by reference. Thus, a preferred Tnp of the present invention includes an amino acid other than methionine at amino acid position 56 to ensure the absence of the inhibitor from the in vitro system of the present invention (described below). However, it should be noted a position 56 modification is not essential to the present invention because other means can be used to eliminate the inhibitor from the in vitro system. For example, the inhibitor protein can be separated from a Tn5 Tnp according to differences in size between the two proteins.

It is appreciated that additional amino acid sequences can be added to the N-terminus, C-terminus or both of a Tnp of the present invention without reducing the transposase activity to the level of the wild-type enzyme. A polypeptide or isolated polypeptide comprising a Tnp of the present invention flanked by the additional amino acid sequences as described above is within the scope of the present invention. A flanking amino acid sequence can but does not have to assist in purification, detection, or stabilization of the Tnp of the present invention.

In another aspect, the present invention relates to a nucleic acid or isolated nucleic acid that comprises a nucleotide sequence encoding a Tnp of the present invention. The nucleic acid can further comprise a native or non-native transcription control sequence (e.g., a promoter) operably linked to the coding nucleotide sequence. In addition, the present invention also encompasses a host cell that comprises a nucleic acid of the present invention.

In another aspect, the present invention relates to a system for transposing a transposable DNA sequence in vitro. The system includes a polypeptide that comprises the amino acid sequence of a Tnp of the present invention, a donor DNA molecule comprising the transposable DNA sequence that is flanked at its 5'- and 3'-ends by wild-type Tn5 OE sequences, wild-type Tn5 IE sequences, or modified Tn5 OE sequences that are active for in vitro transposition (defined below), and a target DNA molecule into which the transposable sequence can transpose.

In a related aspect, the present invention relates to a method of in vitro transposition using the transposition system described above. The method involves combining the donor DNA, the target DNA, and the polypeptide that comprises the amino acid sequence of a Tnp of the present invention in a suitable reaction buffer under suitable transposition conditions for a period of time sufficient for the Tnp to catalyze the in vitro transposition. Details on suitable reaction buffers and reaction conditions are described in U.S. Pat. No. 5,925,545 and Goryshin, I. Y., and Reznikoff, W. S., "Tn5 in vitro transposition," *J. Biol. Chem.* 273:7367-7374 (1998), incorporated by reference as if set forth herein in its entirety. Although in U.S. Pat. No. 5,925,545 and Goryshin and Reznikoff (1998) the in vitro transposition was carried out with a two-step temperature incubation (below physiological temperature for binding of transposase to OE and physiological temperature for transposition), it is noted here that the whole procedure can also be carried out at one temperature (e.g., a physiological temperature).

The donor DNA can be circular or linear. If the donor DNA is linear, the OE sequences flanking the transposable DNA sequence can be at the termini of the linear donor DNA or the donor DNA can include some nucleotides upstream and downstream from the OE sequences.

Examples of modified OE sequences that confer an in vitro transposition frequency at least as high as the wild-type sequence are described in U.S. Pat. No. 5,925,545. Other modified OE sequences not specifically described in U.S. Pat. No. 5,925,545 can also be used as long as the combination of a sequence and a Tnp of the present invention results in a detectable level of transposition in vitro. Such modified OE sequences are referred to as modified OE sequences that are active for in vitro transposition and can be readily identified by a skilled artisan using the screening method disclosed in U.S. Pat. No. 5,925,545.

The transposable DNA sequence between the OE sequences can include any desired nucleotide sequence. The length of the transposable DNA sequence between the OE sequences should be at least about 50 nucleotides, although smaller inserts may work. No upper limit to the insert size is known. However, it is known that a transposable DNA sequence of about 300 nucleotides in length can function well. By way of non-limiting examples, the transposable DNA sequence can include a coding region that encodes a detectable or selectable protein, with or without associated regulatory elements such as promoter, terminator, or the like.

If the transposable DNA sequence includes such a detectable or selectable coding region without a promoter, it will be possible to identify and map promoters in the target DNA that are uncovered by transposition of the coding region into a position downstream thereof, followed by analysis of the nucleic acid sequences upstream from the transposition site.

Likewise, the transposable DNA sequence can include a primer binding site that can be transposed into the target DNA, to facilitate sequencing methods or other methods that rely upon the use of primers distributed throughout the target genetic material. Similarly, the method can be used to introduce a desired restriction enzyme site or polylinker, or a site suitable for another type of recombination, such as a cre-lox, into the target.

The target DNA into which a transposable DNA sequence is transposed does not have any specific sequence requirements. Wild-type Tn5 Tnp has few, if any, preference for insertion sites. The Tnps of the present invention are likewise believed to exhibit no preference for insertion sites. Accordingly, the method of the present invention can introduce changes into any target DNA.

In another aspect, the present invention relates to a method of using a Tnp of the present invention for in vitro intramolecular transpositions as described in U.S. Pat. No. 5,948,622. The molecule involved in this method is a genetic construct that comprises a transposable portion and a donor backbone portion. The transposable portion comprises an origin of replication, a nucleotide sequence of interest, and a pair of the wild-type Tn5 OE sequences, the wild-type Tn5 IE sequences, or modified Tn5 OE sequences that are active for in vitro transposition. The method involves combining, in an in vitro reaction mix, a polypeptide that comprises the amino acid sequence of a Tnp of the present invention with the genetic construct described above at a low concentration, to generate reaction products, transforming the reaction products into a host cell, proliferating the host cell to obtain multiple transformed cells, and selecting from among the multiple transformed cells for cells that contain a DNA molecule that has lost the donor backbone portion and that contain the nucleotide sequence of interest that has been transposed. By low concentration, we mean that the genetic construct's concentration is sufficiently low so that intramolecular transposition, as opposed to intermolecular transposition, is encouraged. A skilled artisan can readily determine the suitable low concentrations for a particular application. Generally speaking, the applicants have found a suitable amount of nucleic acid to be in the range of 0.05-0.005 µg/µl of reaction mix. At 0.05 µg/µl, 95% of the transposition events are intramolecular. At 0.005 µg/µl, or lower, about 100% of the events are intramolecular transpositions. Details on how to practice the method are described in U.S. Pat. No. 5,948,622.

In another aspect, the present invention relates to a method for forming a synaptic complex in vitro between a polypeptide that comprises an amino acid sequence of a Tnp of the present invention and a polynucleotide that comprises a transposable nucleotide sequence flanked by a pair of the wild-type Tn5 OE sequences, the wild-type Tn5 IE sequences, or modified OE sequences that are active for in vitro transposition. The method involves combining the polypeptide with the polynucleotide in vitro under conditions that disfavor polynucleotide strand transfer. The synaptic complex formed can be introduced into a target cell under suitable conditions to make an insertional mutation at a random or quasi-random position in the cellular nucleic acid. By making an insertional mutation at a quasi-random position, we mean that the insertion event has a slight preference for one sequence over another. Details on how to form the synaptic complex and how to introduce the complex into a cell to make insertional mutations are described in U.S. Pat. No. 6,159,736.

The present invention will be more readily understood upon consideration of the following examples which are exemplary and are not intended to limit the scope of the invention.

EXAMPLE 1

Construction of Modified (Mutated) Tn5 Tnps

The strategy used to create these modified Tn5 Tnps was based on the Stratagene Quikchange Kit (La Jolla, Calif.). Primers were complementary to the top and bottom strand of the region to be mutagenized, with the point mutation located at least 10 bases from the end of the 25-45 base primer (ordered from Integrated DNA Technology, Coralville, Iowa). Polymerase chain reactions were used to amplify the entire plasmid. The PCR was carried out as follows: 100 ng of each primer was mixed with 50 ng template DNA, 25 mM each dNTP, 10× reaction buffer, and 2.5 U of Pfu Turbo. The reaction was diluted to a final volume of 50 µL. This reaction was then placed in a thermocycler, heated to 94° C. for 1 minute and then cycled 19 times as follows: 1) 30 seconds at 95° C., 2) 1 minute at 55° C., and 3) 1 minute/kb of plasmid (10 minutes) at 72° C. This cycle was followed by a final 5 minute extension reaction at 72° C. The amplification creates mutated, plasmid DNA with staggered nicks. Following PCR amplification, DNA was purified from the reaction mixture using the Qiagen PCR cleaning kit (Valencia, Calif.). This DNA was then digested with Dpn 1 for 1 hour at 37° C. Dpn 1 restriction enzyme only reacts with methylated DNA strands, and therefore, will only leave the template DNA (which is host methylated). Following digestion, the reaction mixtures were dialyzed for 1 hour on Millipore 0.05 µM filters, against ddH$_2$O. The dialyzed DNA samples were transformed into DH5α *E. coli* cells via electroporation, and the mutagenized plasmids were selected for their resistance to Amp.

EXAMPLE 2

In Vivo Transposition with Modified Tn5 Tnps

Fifteen modified Tn5 Tnps were tested for their transposition activity. The name and modifications or mutations (relative to the wild-type Tn5 Tnp) of each of the modified Tn5 Tnps are listed in Table 1. The EK/LP mutant is known to be hyperactive in comparison to the wild-type Tn5 Tnp and was used as a control in the assay.

Qualitative in vivo assay of the modified Tn5 Tnps: To begin characterizing the modified Tn5 Tnps, in vivo transposition activity was assessed using a qualitative papillation assay as described in Krebs, M. P., and Reznikoff, W. S. (1988) Gene 63, 277-285, herein incorporated by reference in its entirety. With this assay, a plasmid expressing EK/LP or another modified Tn5 Tnp was electroporated into a recA$^-$ lac$^-$ strain that contains pOX386, an F factor. This F factor encodes a transposon that has a Tetr gene, a promoterless lacZ gene (lacking a Shine-Dalgamo sequence), and is defined by inverted 19 bp OEs. When a functional Tnp was provided in trans, the transposon would induce transposition and move from pOX386 (including the promoterless lazZ gene) to the chromosome. If the transposon integrated downstream of a functional promoter in the correct reading frame and orientation, β-galactosidase mRNA would be translated. The cell would then be able to use lactose or PG (Phenyl-β-D-galactoside) as a sugar source. Because these cells possessed a growth advantage, they would appear as papilli in the larger colony. If X-gal was included in the media, the papilli would be blue.

Modified Tn5 Tnps cloned into pTYB4 (cysteine (−) background) were used for the assay. PTYB4 was obtained from New England Biolabs (Beverly, Mass.). Plasmids expressing modified Tn5 Tnps (intein-fusion) were transformed into the papillation strain and an appropriate number of cells were plated on glucose minimal media containing X-gal, PG, Amp$^{100}$, and Tet$^{15}$. Single colonies were replica plated onto the same media to give each colony equal space and resources. The plates were incubated at 30° C. and were observed each day for papilliation.

Qualitative analysis of the papillation screen shows that Y41A, S42A, Y41C, W450C, E451C, and E454C Tnps displayed transposition frequencies comparable to or higher than that of the EK/LP mutant (Table 1). K40A, K44A, and K44C Tnps displayed transposition frequencies lower than that of the EK/LP mutant (Table 1). No transposition was observed for A39D, W453C, and Y41C—W453C Tnps (Table 1).

TABLE 1

In vitro transposition frequency of varius modified Tn5 Tnps (more plus signs indicate higher transposition frequency).

| Mutant Name | Mutations (modifications) Present | In vivo Transposition Frequency |
|---|---|---|
| EK/LP | E54K, M56A, L372P | "+++" |
| A39D | E54K, M56A, L372P, A39D | None |
| A39S | E54K, M56A, L372P, A39S | "+++" |
| K40A | E54K, M56A, L372P, K40A | "++" |
| Y41A | E54K, M56A, L372P, Y41A | "++++" |
| S42A | E54K, M56A, L372P, S42A | "++++" |
| K44A | E54K, M56A, L372P, K44A | "++" |
| Y41C | E54K, M56A, L372P, C187A, C402A, Y41C | "++++" |
| K44C | E54K, M56A, L372P, C187A, C402A, K44C | "++" |
| W450C | E54K, M56A, L372P, C187A, C402A, W450C | "++++++" |
| E451C | E54K, M56A, L372P, C187A, C402A, E451C | "++++" |
| W453C | E54K, M56A, L372P, C187A, C402A, W453C | None |
| E454C | E54K, M56A, L372P, C187A, C402A, E454C | "++++" |
| Y41C-W450C | E54K, M56A, L372P, C187A, C402A, Y41C, W450C | "++++++" |
| Y41C-W453C | E54K, M56A, L372P, C187A, C402A, Y41C, W453C | None |

EXAMPLE 3

In Vitro Transposition with Modified Tn5 Tnps

Five modified Tn5 Tnps were tested for their transposition activity: EK/LP, Y41A, S42A, W450C, and E454C. The modifications or mutations (relative to the wild-type Tn5 Tnp) on each of the modified Tn5 Tnps can be found in Table 1.

Quantitative in vitro assay of the modified Tn5 Tnps: In vitro transposition activity was assessed using the general in vitro assay. In this reaction, 32 pmol of substrate DNA (TL1 or TL2) was added to 1.1 nmol of protein (EK/LP or other modified Tn5 Tnps) in transposition buffer (10 mM magnesium acetate, 100 mM potassium glutamate, 20 mM HEPES, pH 7.5). TL1 and TL2 correspond to the outside end (OE) and inside end (IE) recognition sequence, respectively (Goryshin, I. Y., and Reznikoff, W. S. (1998), J. Biol. Chem. 273, 7367-7374; and Zhou, M., Bhasin, A, and Reznikoff, W. S. (1998) J. Mol. Biol. 276, 913-925, both of which are herein incorporated by reference in their entirety). This mixture was allowed to incubate at 37° C. for 90 minutes. Aliquots (5 μL) were taken and were added to 2.5 μL 1% SDS to remove the protein from the DNA. The reaction products were then visualized by 1% agarose gel electrophoresis. Percent of remaining substrate was calculated as follows using Molecular Dynamics Image Quant software: % remaining substrate=(% substrate)/(% substrate+% linear+% donor backbone).

The results of this assay are shown in Table 2. In all instances, the modified protein metabolizes more of the substrate (less % substrate remains after 90 minutes) as compared to the EZ/LP control protein. The W450C protein is particularly hyperactive. Additionally, TL1 corresponds to the OE recognition sequence and TL2 corresponds to the IE recognition sequence. It is important to note that none of the modified proteins show a dramatic bias for either end sequence (whereas EK/LP shows a preference for OE). This indicates that the mutations are not change of specificity mutations, and are therefore, not involved in DNA recognition.

TABLE 2

| | Percent of remaining substrate. | | | | |
|---|---|---|---|---|---|
| | EK/LP | Y41A | S42A | W450C | E454C |
| TL1 | 30.3 | 20.1 | 29.8 | 10.3 | 26.6 |
| TL2 | 49.3 | 18.5 | 25.4 | 9.2 | 34.9 |

The foregoing examples are not intended to limit the scope of the invention. Rather the invention is understood to encompass all the variations and modifications that come within the scope of the appended claims.

We claim:

1. An isolated polypeptide comprising SEQ ID NO:2 modified at an amino acid position selected from the group consisting of position 42, position 450, and position 454, wherein the polypeptide with said modification has greater avidity than wild-type Tn5 transposase (SEQ ID NO:2) for at least one of a Tn5 outside end sequence as defined by SEQ ID NO:3, a Tn5 inside end sequence as defined by SEQ ID NO:4, and a modified Tn5 outside end sequence as defined by SEQ ID NO:5.

2. An isolated polypeptide as claimed in claim 1 wherein the amino acid sequence is modified by an amino acid substitution.

3. An isolated polypeptide as claimed in claim 2 wherein amino acid 42 is substituted by an alanine.

4. An isolated polypeptide as claimed in claim 2 wherein amino acid 450 is substituted by a cysteine.

5. An isolated polypeptide as claimed in claim 2 wherein amino acid 454 is substituted by a cysteine.

6. An isolated polypeptide comprising SEQ ID NO:2 modified at amino acid position 451 and modified at an amino acid position selected from the consisting of position 42, position 450, and position 454, wherein the polypeptide with said modification has greater avidity than wild-type Tn5 transposase (SEQ ID NO:2) for at least one of a Tn5 outside end sequence as defined by SEQ ID NO:3, a Tn5 inside end sequence as defined by SEQ ID NO:4, and a modified Tn5 outside end sequence as defined by SEQ ID NO:5.

7. An isolated polypeptide as claimed in claim 6 wherein amino acid 451 is modified by a substitution.

8. An isolated polypeptide as claimed in claim 7 wherein amino acid 451 is substituted by a cysteine.

9. An isolated polypeptide comprising SEQ ID NO:2 modified at amino acid position 372 and modified at an amino acid position selected from the group consisting of position 42, position 450, and position 454, wherein the polypeptide with said modification has greater avidity than wild-type Tn5 transposase (SEQ ID NO:2) for at least one of a Tn5 outside end sequence as defined by SEQ ID NO:3, a Tn5 inside end sequence as defined by SEQ ID NO:4, and a modified Tn5 outside end sequence as defined by SEQ ID NO:5.

10. An isolated polypeptide comprising SEQ ID NO:2 modified at an amino acid position selected from the group consisting of position 54 and position 56 and modified at an amino acid position selected from the group consisting of position 42, position 450, and position 454, wherein the polypeptide with said modification has greater avidity than wild-type Tn5 transposase (SEQ ID NO:2) for at least one of a Tn5 outside end sequence as defined by SEQ ID NO:3, a Tn5 inside end sequence as defined by SEQ ID NO:4, and a modified Tn5 outside end sequence as defined by SEQ ID NO:5.

11. An isolated polypeptide as claimed in claim 1 wherein the polypeptide consists of SEQ ID NO:2 modified at an amino acid position selected from the group consisting of position 42, position 450, and position 454.

12. A system for transposing a transposable DNA sequence in vitro, the system comprising:
   the polypeptide of claim 1;
   a donor DNA molecule comprising the transposable DNA sequence, the transposable DNA sequence being flanked at its 5'- and 3'-ends by sequences selected from the group consisting of a wild-type Tn5 outside end sequence, a wild-type Tn5 inside end sequence, and a modified Tn5 outside end sequence that is active for in vitro transposition; and
   a target DNA molecule into which the transposable DNA sequence can transpose.

13. A method for in vitro transposition, the method comprising the step of:
   combining a donor DNA molecule that comprises a transposable DNA sequence of interest with a target DNA molecule and the polypeptide of claim 1 in a suitable reaction buffer for a period of time sufficient for the enzyme to catalyze in vitro transposition,
   wherein the transposable DNA sequence of interest is flanked at its 5'- and 3'-ends by a pair of outside end sequences selected from the group consisting of a wild-type Tn5 outside end sequence, a wild-type Tn5 inside end sequence, and a modified Tn5 outside end sequence that is active for in vitro transposition.

14. A method for in vitro transposition in a genetic construct that comprises a transposable portion and a donor backbone portion, the transposable portion comprising an origin of replication, a nucleotide sequence of interest, and a pair of outside end sequences flanking the donor backbone portion, the outside end sequences are selected from the group consisting of a wild-type Tn5 outside end sequence, a wild-type Tn5 inside end sequence, and a modified Tn5 outside end sequence that is active for in vitro transposition, the method comprising the steps of:
   combining, in an in vitro reaction mix, the polypeptide of claim 1 and the genetic construct at a low concentration, to generate reaction products;
   transforming the reaction products into a host cell;
   proliferating the host cell to generate multiple transformed cells; and
   selecting from among the multiple transformed cells for cells that comprise (i) a DNA molecule that has lost the donor backbone portion and (ii) the nucleotide sequence of interest that has been transposed.

15. A method for forming a synaptic complex between (i) the polypeptide of claim 1 and (ii) a polynucleotide that comprises a pair of outside end sequences and a transposable nucleotide sequence there between, wherein the outside sequences are selected from the group consisting of a wild-type Tn5 outside end sequence, a wild-type Tn5 inside end sequence, and a modified Tn5 outside end sequence that is active for in vitro transposition, the method comprising the step of:
   combining (i) and (ii) in vitro under conditions that disfavor polynucleotide strand transfer to form the synaptic complex.

* * * * *

UNITED STATES PATENT AND TRADEMARK OFFICE
CERTIFICATE OF CORRECTION

PATENT NO. : 7,608,434 B2 Page 1 of 1
APPLICATION NO. : 11/195113
DATED : October 27, 2009
INVENTOR(S) : Reznikoff et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 680 days.

Signed and Sealed this

Twelfth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,608,434 B2
APPLICATION NO. : 11/195113
DATED : October 27, 2009
INVENTOR(S) : William S. Reznikoff et al.

Page 1 of 1

It is certified that error appears in the above-identified patent and that said Letters Patent is hereby corrected as shown below:

In the Specification

Column 1, Lines 14-17:
Delete the phrase:
"This invention was made with United States government support awarded by the following agency: NIH, Grant No. GM50692. The United States government has certain rights in this invention."

And replace with:
--This invention was made with government support under GM050692 awarded by the National Institutes of Health. The government has certain rights in the invention.--.

Signed and Sealed this
Eighth Day of December, 2020

Andrei Iancu
*Director of the United States Patent and Trademark Office*

SEQUENCE LISTING

<160> NUMBER OF SEQ ID NOS: 5

<210> SEQ ID NO 1
<211> LENGTH: 1431
<212> TYPE: DNA
<213> ORGANISM: Escherichia coli
<220> FEATURE:
<221> NAME/KEY: CDS
<222> LOCATION: (1)..(1428)

<400> SEQUENCE: 1

```
atg ata act tct gct ctt cat cgt gcg gcc gac tgg gct aaa tct gtg      48
Met Ile Thr Ser Ala Leu His Arg Ala Ala Asp Trp Ala Lys Ser Val
1               5                  10                  15 ttc tct tcg gcg gcg ctg ggt gat cct cgc cgt act gcc cgc ttg gtt      96
Phe Ser Ser Ala Ala Leu Gly Asp Pro Arg Arg Thr Ala Arg Leu Val
            20                  25                  30 aac gtc gcc gcc caa ttg gca aaa tat tct ggt aaa tca ata acc atc     144
Asn Val Ala Ala Gln Leu Ala Lys Tyr Ser Gly Lys Ser Ile Thr Ile
        35                  40                  45 tca tca gag ggt agt gaa gcc atg cag gaa ggc gct tac cga ttt atc     192
Ser Ser Glu Gly Ser Glu Ala Met Gln Glu Gly Ala Tyr Arg Phe Ile
    50                  55                  60 cgc aat ccc aac gtt tct gcc gag gcg atc aga aag gct ggc gcc atg     240
Arg Asn Pro Asn Val Ser Ala Glu Ala Ile Arg Lys Ala Gly Ala Met
65                  70                  75                  80 caa aca gtc aag ttg gct cag gag ttt ccc gaa ctg ctg gcc att gag     288
Gln Thr Val Lys Leu Ala Gln Glu Phe Pro Glu Leu Leu Ala Ile Glu
                85                  90                  95 gac acc acc tct ttg agt tat cgc cac cag gtc gcc gaa gag ctt ggc     336
Asp Thr Thr Ser Leu Ser Tyr Arg His Gln Val Ala Glu Glu Leu Gly
            100                 105                 110 aag ctg ggc tct att cag gat aaa tcc cgc gga tgg tgg gtt cac tcc     384
Lys Leu Gly Ser Ile Gln Asp Lys Ser Arg Gly Trp Trp Val His Ser
        115                 120                 125 gtt ctc ttg ctc gag gcc acc aca ttc cgc acc gta gga tta ctg cat     432
```

```
                Val Leu Leu Leu Glu Ala Thr Thr Phe Arg Thr Val Gly Leu Leu His
                    130                 135                 140 cag gag tgg tgg atg cgc ccg gat gac cct gcc gat gcg gat gaa aag          480
Gln Glu Trp Trp Met Arg Pro Asp Asp Pro Ala Asp Ala Asp Glu Lys
145                 150                 155                 160 gag agt ggc aaa tgg ctg gca gcg gcc gca act agc cgg tta cgc atg          528
Glu Ser Gly Lys Trp Leu Ala Ala Ala Ala Thr Ser Arg Leu Arg Met
                165                 170                 175 ggc agc atg atg agc aac gtg att gcg gtc tgt gac cgc gaa gcc gat          576
Gly Ser Met Met Ser Asn Val Ile Ala Val Cys Asp Arg Glu Ala Asp
                180                 185                 190 att cat gct tat ctg cag gac aaa ctg gcg cat aac gag cgc ttc gtg          624
Ile His Ala Tyr Leu Gln Asp Lys Leu Ala His Asn Glu Arg Phe Val
                195                 200                 205 gtg cgc tcc aag cac cca cgc aag gac gta gag tct ggg ttg tat ctg          672
Val Arg Ser Lys His Pro Arg Lys Asp Val Glu Ser Gly Leu Tyr Leu
        210                 215                 220 tac gac cat ctg aag aac caa ccg gag ttg ggt ggc tat cag atc agc          720
Tyr Asp His Leu Lys Asn Gln Pro Glu Leu Gly Gly Tyr Gln Ile Ser
225                 230                 235                 240 att ccg caa aag ggc gtg gtg gat aaa cgc ggt aaa cgt aaa aat cga          768
Ile Pro Gln Lys Gly Val Val Asp Lys Arg Gly Lys Arg Lys Asn Arg
                245                 250                 255 cca gcc cgc aag gcg agc ttg agc ctg cgc agt ggg cgc atc acg cta          816
Pro Ala Arg Lys Ala Ser Leu Ser Leu Arg Ser Gly Arg Ile Thr Leu
                260                 265                 270 aaa cag ggg aat atc acg ctc aac gcg gtg ctg gcc gag gag att aac          864
Lys Gln Gly Asn Ile Thr Leu Asn Ala Val Leu Ala Glu Glu Ile Asn
                275                 280                 285 ccg ccc aag ggt gag acc ccg ttg aaa tgg ttg ttg ctg acc agc gaa          912
Pro Pro Lys Gly Glu Thr Pro Leu Lys Trp Leu Leu Leu Thr Ser Glu
290                 295                 300 ccg gtc gag tcg cta gcc caa gcc ttg cgc gtc atc gac att tat acc          960
Pro Val Glu Ser Leu Ala Gln Ala Leu Arg Val Ile Asp Ile Tyr Thr
305                 310                 315                 320 cat cgc tgg cgg atc gag gag ttc cat aag gca tgg aaa acc gga gca         1008
His Arg Trp Arg Ile Glu Glu Phe His Lys Ala Trp Lys Thr Gly Ala
                325                 330                 335 gga gcc gag agg caa cgc atg gag gag ccg gat aat ctg gag cgg atg         1056
Gly Ala Glu Arg Gln Arg Met Glu Glu Pro Asp Asn Leu Glu Arg Met
                340                 345                 350 gtc tcg atc ctc tcg ttt gtt gcg gtc agg ctg tta cag ctc aga gaa         1104
Val Ser Ile Leu Ser Phe Val Ala Val Arg Leu Leu Gln Leu Arg Glu
                355                 360                 365 agc ttc acg ctg ccg caa gca ctc agg gcg caa ggg ctg cta aag gaa         1152
Ser Phe Thr Leu Pro Gln Ala Leu Arg Ala Gln Gly Leu Leu Lys Glu
        370                 375                 380 gcg gaa cac gta gaa agc cag tcc gca gaa acg gtg ctg acc ccg gat         1200
Ala Glu His Val Glu Ser Gln Ser Ala Glu Thr Val Leu Thr Pro Asp
385                 390                 395                 400 gaa tgt cag cta ctg ggc tat ctg gac aag gga aaa cgc aag cgc aaa         1248
Glu Cys Gln Leu Leu Gly Tyr Leu Asp Lys Gly Lys Arg Lys Arg Lys
                405                 410                 415 gag aaa gca ggt agc ttg cag tgg gct tac atg gcg ata gct aga ctg         1296
Glu Lys Ala Gly Ser Leu Gln Trp Ala Tyr Met Ala Ile Ala Arg Leu
                420                 425                 430 ggc ggt ttt atg gac agc aag cga acc gga att gcc agc tgg ggc gcc         1344
Gly Gly Phe Met Asp Ser Lys Arg Thr Gly Ile Ala Ser Trp Gly Ala
        435                 440                 445
```

```
ctc tgg gaa ggt tgg gaa gcc ctg caa agt aaa ctg gat ggc ttt ctt    1392
Leu Trp Glu Gly Trp Glu Ala Leu Gln Ser Lys Leu Asp Gly Phe Leu
    450                 455                 460 gcc gcc aag gat ctg atg gcg cag ggg atc aag atc tga                1431
Ala Ala Lys Asp Leu Met Ala Gln Gly Ile Lys Ile
465                 470                 475
```

<210> SEQ ID NO 2
<211> LENGTH: 476
<212> TYPE: PRT
<213> ORGANISM: Escherichia coli

<400> SEQUENCE: 2

```
Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
        50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
        195                 200                 205

Val Arg Ser Lys His Pro Arg Lys Asp Val Glu Ser Gly Leu Tyr Leu
    210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
        275                 280                 285

Pro Pro Lys Gly Glu Thr Pro Leu Lys Trp Leu Leu Leu Thr Ser Glu
    290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335
```

-continued

```
Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
        355                 360                 365

Ser Phe Thr Leu Pro Gln Ala Leu Arg Ala Gln Gly Leu Leu Lys Glu
    370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
    450                 455                 460

Ala Ala Lys Asp Leu Met Ala Gln Gly Ile Lys Ile
465                 470                 475

<210> SEQ ID NO 3
<211> LENGTH: 19
<212> TYPE: DNA
<213> ORGANISM: Escherichia coli

<400> SEQUENCE: 3
ctgactctta tacacaagt                                               19

<210> SEQ ID NO 4
<211> LENGTH: 19
<212> TYPE: DNA
<213> ORGANISM: Escherichia coli

<400> SEQUENCE: 4
ctgtctcttg atcagatct                                               19

<210> SEQ ID NO 5
<211> LENGTH: 19
<212> TYPE: DNA
<213> ORGANISM: Escherichia coli

<400> SEQUENCE: 5
ctgtctctta tacacatct                                               19
```